(12) United States Patent
Justis

(10) Patent No.: US 7,497,869 B2
(45) Date of Patent: Mar. 3, 2009

(54) METHODS AND DEVICES FOR A MINIMALLY INVASIVE PLACEMENT OF A ROD WITHIN A PATIENT

(75) Inventor: Jeff R. Justis, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 387 days.

(21) Appl. No.: 11/341,189

(22) Filed: Jan. 27, 2006

(65) Prior Publication Data

US 2007/0191836 A1    Aug. 16, 2007

(51) Int. Cl.
*A61B 18/14* (2006.01)
*A61F 5/00* (2006.01)

(52) U.S. Cl. ................................ 606/279; 606/86 R

(58) Field of Classification Search .............. 606/246, 606/256, 264, 265, 279, 99, 104, 103, 914, 606/86 R See application file for complete search history.

(56) References Cited

U.S. PATENT DOCUMENTS

| | | | |
|---|---|---|---|
| 5,584,833 A | 12/1996 | Fournet-Fayard et al. | |
| 5,593,407 A | 1/1997 | Reis | |
| 5,649,947 A | 7/1997 | Auerbach et al. | |
| 5,707,372 A | 1/1998 | Errico et al. | |
| 5,716,355 A | 2/1998 | Jackson et al. | |
| 5,725,536 A | 3/1998 | Oberlin et al. | |
| 5,738,685 A | 4/1998 | Halm et al. | |
| 5,752,957 A | 5/1998 | Ralph et al. | |
| 5,885,284 A | 3/1999 | Errico et al. | |
| 6,033,406 A | 3/2000 | Mathews | |
| 6,033,411 A * | 3/2000 | Preissman | 606/99 |
| 6,287,313 B1 | 9/2001 | Sasso | |
| 6,342,056 B1 | 1/2002 | Mac-Thiong et al. | |
| 6,443,953 B1 | 9/2002 | Perra et al. | |
| 6,530,929 B1 * | 3/2003 | Justis et al. | 606/103 |
| 6,802,844 B2 | 10/2004 | Ferree | |
| 6,923,811 B1 | 8/2005 | Carl et al. | |
| 2002/0058942 A1 | 5/2002 | Biedermann et al. | |
| 2004/0039384 A1 | 2/2004 | Boehm, Jr. et al. | |
| 2004/0215190 A1 | 10/2004 | Nguyen et al. | |
| 2005/0038432 A1 | 2/2005 | Shaolian et al. | |
| 2005/0215999 A1 | 9/2005 | Birkmeyer et al. | |
| 2005/0234449 A1 | 10/2005 | Aferzon | |
| 2006/0009777 A1 | 1/2006 | Lim et al. | |
| 2008/0082103 A1 * | 4/2008 | Hutton et al. | 606/73 |
| 2008/0091213 A1 * | 4/2008 | Jackson | 606/99 |
| 2008/0125788 A1 * | 5/2008 | Cohen et al. | 606/104 |

FOREIGN PATENT DOCUMENTS

| | | |
|---|---|---|
| DE | 19841651 A1 | 3/2000 |
| WO | 2005060534 A2 | 7/2005 |
| WO | 2005076868 A2 | 8/2005 |
| WO | WO 2005/076868 A2 * | 8/2005 |

* cited by examiner

*Primary Examiner*—Eduardo C Robert
*Assistant Examiner*—Ellen Rust
(74) *Attorney, Agent, or Firm*—Coats & Bennett, PLLC

(57) ABSTRACT

The present application is directed to devices and methods for positioning a rod within a patient. One embodiment of the device may include an elongated inserter having a first end and a second end. A connector may be attached to the second end of the inserter for releasably connecting to the rod. The connector may be adjustable between a first position with the rod substantially coaxially aligned with the inserter, and a second position with the rod substantially perpendicular to the inserter.

20 Claims, 13 Drawing Sheets

METHODS AND DEVICES FOR A MINIMALLY INVASIVE PLACEMENT OF A ROD WITHIN A PATIENT

BACKGROUND

The present application is directed to methods and devices for implanting a rod within a patient and, more specifically, to methods and devices for implanting a rod in a minimally invasive manner.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Vertebral rods may be implanted to support and position the vertebral members in one or more of these regions. The rods extend along a section of the spine and may include a curved configuration to conform to the curvature of the spine. Attachment mechanisms are used to attach the rods to the vertebral members. The attachment mechanisms attach to a vertebral member, and also attach to the rod.

Insertion of the rod into a patient normally requires a large incision through the skin and detachment of the paravertebral muscles to access the vertebral members. This type of procedure usually results in a longer surgical procedure with greater amounts of blood loss and increased anesthesia time. These procedures may also have a higher risk of infection, require a longer postoperative recovery time, and result in addition pain and discomfort to the patient.

SUMMARY

The present application is directed to devices and methods for positioning a vertebral rod within a patient. One embodiment of the device may include an elongated inserter having a first end and a second end. A connector may be attached to the second end of the inserter for releasably connecting to the rod. The connector may be adjustable between a first position with the rod substantially coaxially aligned with the inserter, and a second position with the rod substantially perpendicular to the inserter.

DETAILED DESCRIPTION

The present application is directed to devices and methods for inserting a rod within a patient. In one embodiment, a rod is initially connected to an inserter with a pivoting connection. The connection provides for the rod move from a first position that is aligned with the inserter to a second position that is laterally angled relative to the inserter. The inserter and rod are initially in the aligned first position while being inserted through a guide and into a patient. The rod is then laterally angled outward towards the second position. The second position may provide for positioning the rod within anchors.

Figure 1:
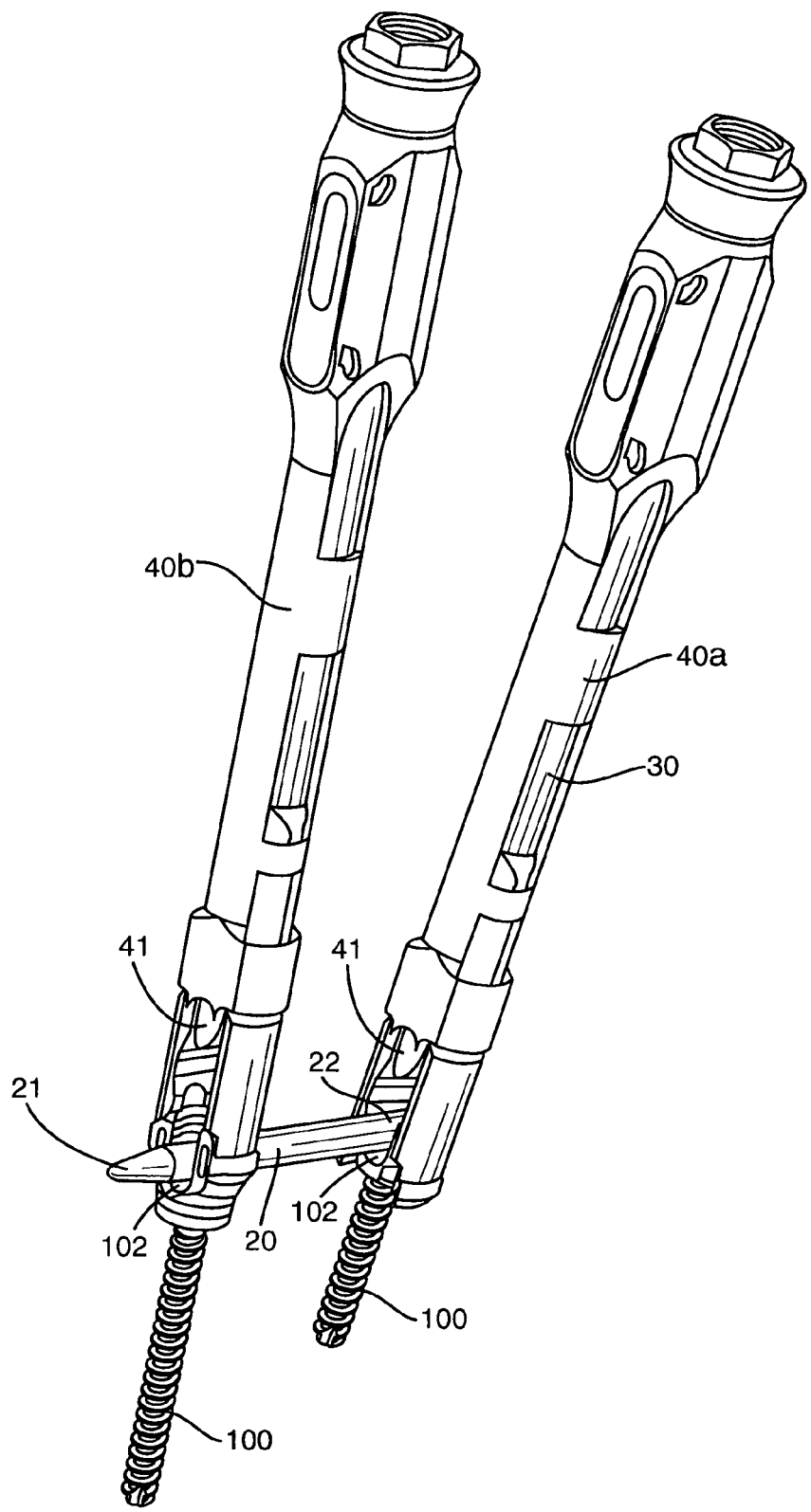
FIG. 1 is a perspective view of a rod extending between anchors according to one embodiment.

FIG. 1 illustrates one embodiment for using the devices and methods. Anchors 100 are secured within the patient with a channel 102 being positioned to receive a rod 20. In one embodiment, the anchors 100 are secured to one or more vertebral members. Guides 40 may be attached to the anchors 100 and provide a conduit for inserting the rod 20 to the anchors 100. The rod 20 and inserter 30 are inserted into the guide 40a. The inserter 30 is manipulated to move the rod 20 through the guide 40a. As the rod 20 approaches a distal end of the guide 40a, the rod 20 pivots outward from the inserter 30 and moves through a slot 41 in the guide 40a. The rod 20 is further pivoted outward with a first end of the rod 20 positioned in the first anchor 100 and the second end in a second anchor 100. After the rod 20 is positioned within the anchors 100, the inserter 30 may be detached from the rod 20 and removed from the guide 40.

Figure 2:
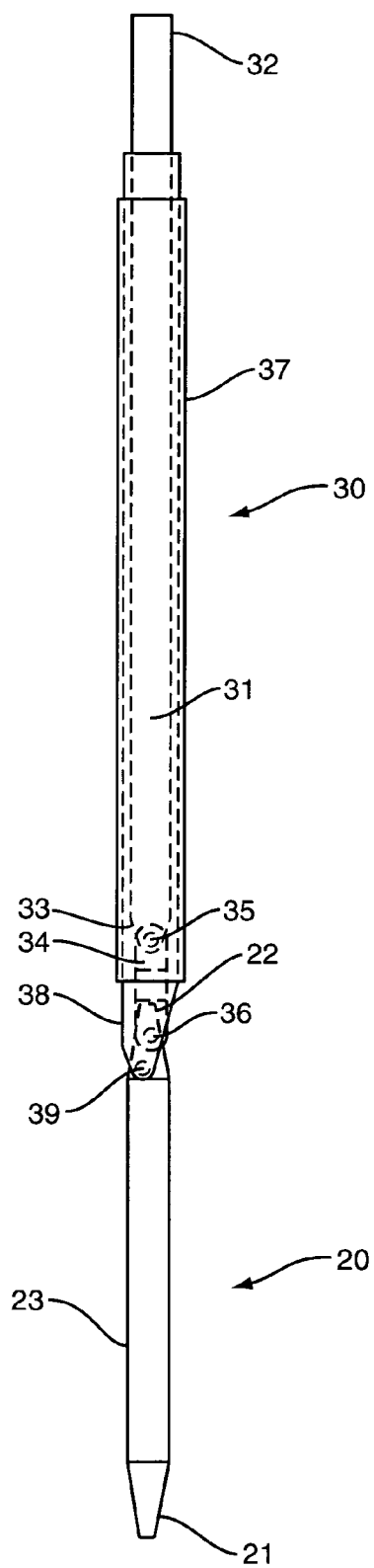
FIG. 2 is a side view of an inserter connected to a rod and positioned in a first orientation according to one embodiment.

FIG. 2 illustrates one embodiment with a rod 20 connected to an inserter 30. Rod 20 has an elongated body 23 that extends between a first end 21 and a second end 22. Rod 20 may have a variety of cross-sectional shapes and sizes, and may have a variety of lengths. In one embodiment, rod 20 has a circular cross-sectional shape. In one embodiment as illustrated in FIG. 2, one or both of the first and second ends 21, 22 may be tapered towards a reduced end. In another embodiment as illustrated in FIGS. 5A-5D, rod 20 has a substantially continuous width throughout.

In one embodiment, inserter 30 has an elongated shape with a width sized to fit within the guide 40. In one embodiment as illustrated in FIG. 2, inserter 30 comprises an elongated member 31 and an exterior sleeve 37. Member 31 has an elongated shape that extends between a proximal end 32 and a distal end 33. In one embodiment as illustrated in FIG. 2, the distal end 33 tapers towards a point. Member 31 may have a variety of shapes and sizes depending upon the context of use. In one embodiment, member 31 is substantially straight. In another embodiment, member 31 may be curved.

In one embodiment, an arm 34 is connected to the distal end 33 of the elongated member 31. The arm 34 is sized to extend outward from the member 31 and connect to the rod 20. In one embodiment, arm 34 includes two opposing sections each positioned on a side of the member 31. A first connector 35 may pivotally connect the arm 34 to the distal end 33 of the member 31. In one embodiment, first connector 35 is a pin that extends through the distal end 33. A second connector 36 connects to the rod 20. In one embodiment, the arm 34 comprises opposing sections each having a ball fitting that mates with an indent in the rod 20 to form the second connector 36. The first and second connectors 35, 36 allow the arm 34 to be pivotally connected to the member 31 and the rod 20.

A sleeve 37 may be positioned over the member 31 and sized to axially move along the member 31. In one embodiment, sleeve 37 includes a cylindrical shape having open distal and proximal ends. In one embodiment, sleeve 37 extends partially around the member 31. An extension 38 may extend outward from the distal end to connect with the rod 20. In one embodiment, extension 38 includes opposing members positioned to contact opposite outer sides of the rod 20.

In one embodiment, extension 38 extends over the arm 34 when the rod 20 and inserter 30 are coaxially aligned as illustrated in FIG. 2. A connector 39 at the end of the extension 38 connects with the rod 20. In one embodiment, connector 39 includes a ball fitting that extends outward from each of the opposing members and seats within detents in the rod 20.

Figure 3:
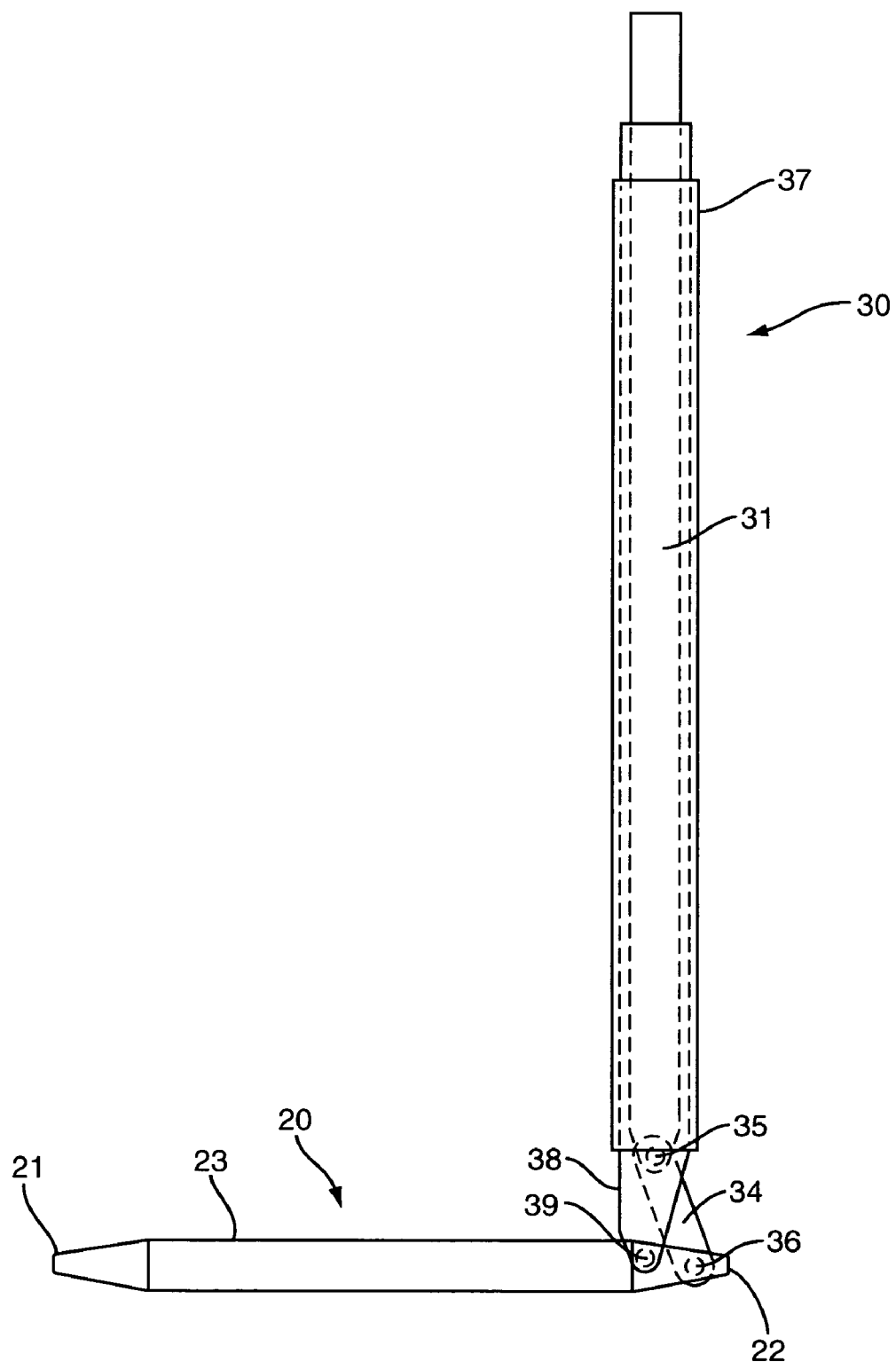
FIG. 3 is a side view of an inserter connected to a rod and positioned in a second orientation according to one embodiment.

Rod 20 is pivotally connected with the inserter 30. In one embodiment, rod 20 is relatively movable between a first orientation as illustrated in FIG. 2 with rod 20 coaxially aligned with the inserter 30, and a second orientation as illustrated in FIG. 3 with the rod 20 that is substantially perpendicular to the inserter 30. In one embodiment, sleeve 37 and extension 38 are axially moved in a proximal direction relative to the member 31 causing the rod 20 to pivot. As best illustrated in FIGS. 2 and 3, the axial movement of the sleeve 37 and extension 38 applies a lifting force to the rod 20 at the connector 39. Connector 39 moves in a proximal direction relative to connector 36. The amount of relative movement between the sleeve 37 and member 31 controls the angle of the rod 20 relative to the inserter 30.

The inserter 30 may be detachable from the rod 20. Detachment of the inserter 30 from the rod 20 may occur in a variety of different manners. In one embodiment, connectors 39 and 36 comprise ball and detent joints. Detents are positioned on the rod 20 at the connection locations. Corresponding ball fittings extend outward from each of the extension 38 and arm 34. The ball and detent connections are sufficient to maintain attachment between the rod 20 and inserter 30 through movement within the guide 40 and moving from the first orientation to the second orientation. A force applied to the inserter 30 in a proximal direction along the guide 40 breaks the connection at each of the connectors 39, 36 and allows removal of the inserter 30.

Another embodiment features the rod 20 having slots that extend into the rod from one of the lateral sides. A first pin extends between two opposing sections that comprise the arm 34, and a second pin extends between two opposing sections that comprise the extension 38. The first pin is positioned within the first slot to form the first connector 36, and the second pin is positioned within the second slot to form the second connector 39. When the rod 20 is coaxially aligned with the inserter 30 as illustrated in FIG. 2, the pins remain within the slots and allow the inserter 30 to position and manipulate the rod 20. When the rod 20 reaches a predetermined angle relative to the inserter 30, the pins slide out from the slots and the rod 20 is detached from the inserter 30. In one embodiment, the rod 20 detaches when it is substantially perpendicular to the inserter 30.

Guide 40 provides a conduit for inserting the rod 20 and accessing the anchors 100. In one embodiment, guide 40 has an outer wall with a hollow interior that is sized to receive the rod 20 and inserter 30. Guide 40 has a length adequate for percutaneous access to the anchor 100 with the distal end positioned at the anchor 100 and the proximal end positioned exterior to the patient. In one embodiment, the distal end of the guide 40 attaches to the anchor 100. In one embodiment, the guide 40 is inserted into a first incision made to the patient. The distal end of the guide 40 is positioned at the member to which the anchor 100 is to be attached. In one embodiment, the guide 40 is inserted with the distal end adjacent to a vertebral member. The anchor 100 is inserted through the guide 40 and attached to the vertebral member. In one embodiment, once the anchor 100 is attached to the vertebral member, the guide 40 is attached to the anchor 100. In another embodiment, the guide 40 remains detached from the anchor 100.

Anchors 100 may have a variety of constructions. In one embodiment, anchors 100 are multi-axial screws having a movable head with a channel 102 for receiving the rod 20. Various other anchors 100 may be employed with the present application.

Figure 4A:
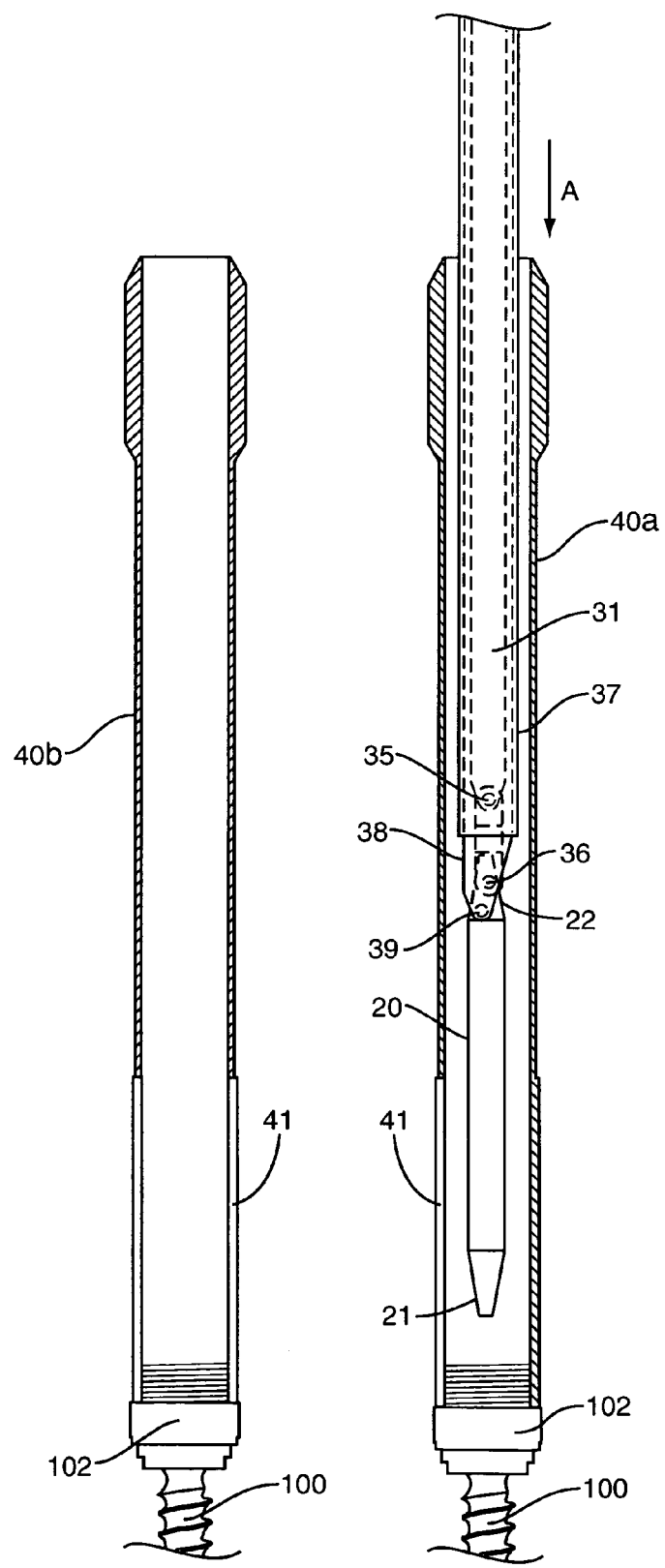
FIGS. 4A-E are side views of inserting a rod to an anchor according to one embodiment.

FIGS. 4A-4E illustrates one embodiment of inserting the rod 20 into the patient. As illustrated in FIG. 4A, the rod 20 is initially attached to the inserter 30. Rod 20 and inserter 30 are moved through the guide 40a in the direction indicated by arrow A towards the anchors 100. In one embodiment, the rod 20 and inserter 30 are coaxially aligned creating a minimum profile for insertion in the guide 40a. In another embodiment, the rod 20 may be out of alignment but still provide a reduced profile to fit within the guide 40a. In one embodiment, the physician grasps a distal end of the inserter 30 and manually inserts the rod 20 and inserter 30 into the guide 40a.

Figure 4B:
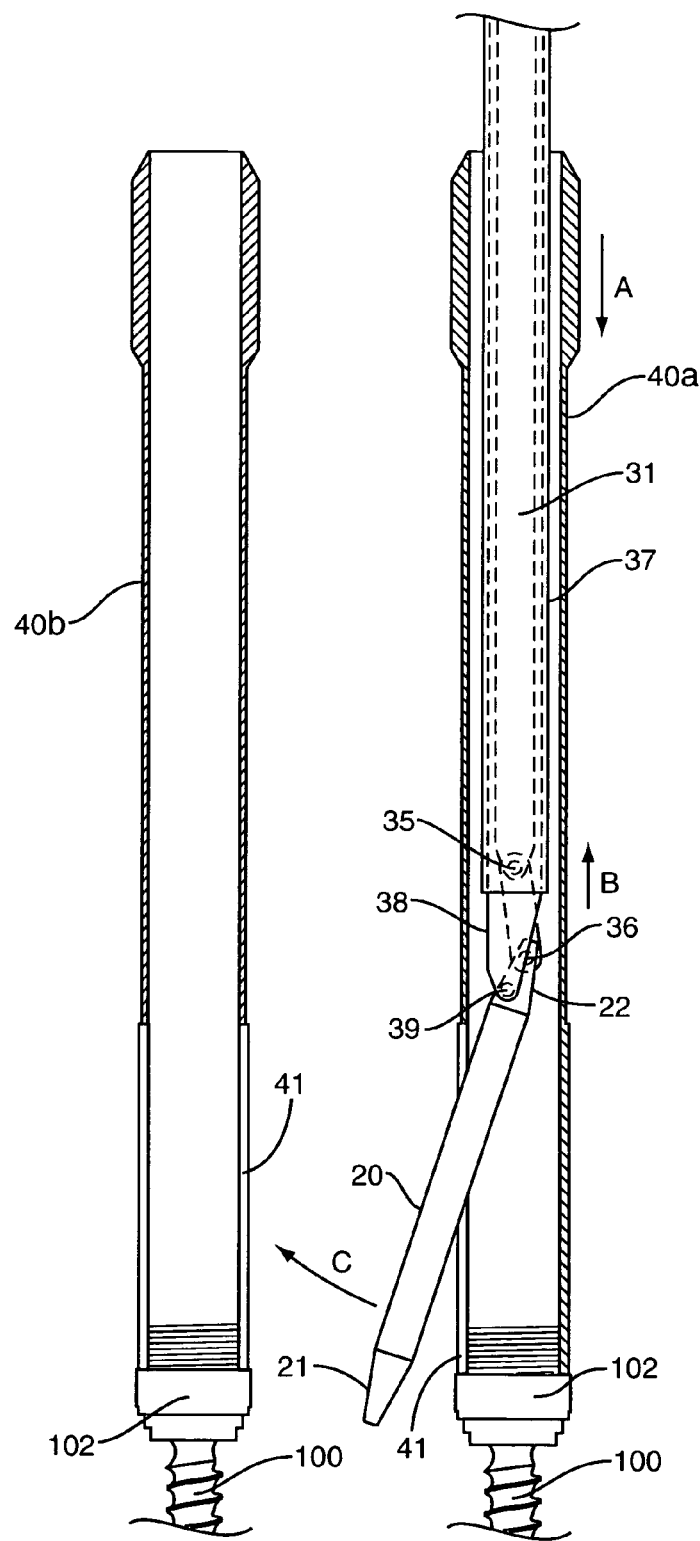
Figure 4C:
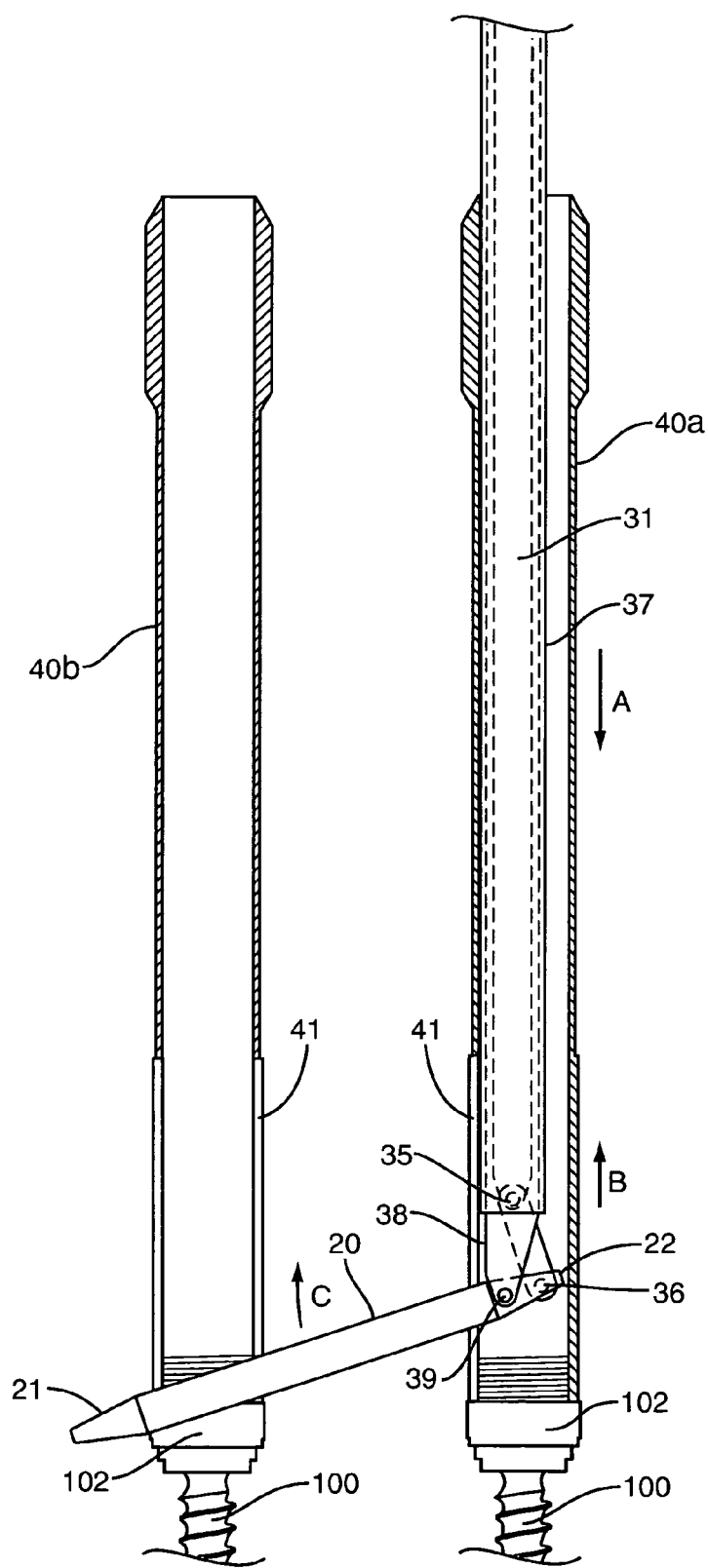

As the rod 20 and inserter 30 continue to move into the guide 40a in the direction of arrow A, the rod 20 is positioned in proximity to a slot 41 at the distal end of the guide 40a. Rod 20 is then pivoted outward in the direction of arrow C as illustrated in FIG. 4B. In one embodiment, this pivoting motion may be caused by axially moving the sleeve 37 in a proximal direction as indicated by arrow B. FIG. 4C illustrates rod 20 pivoted further outward in the direction of arrow C. This continued movement is caused by the proximal movement of sleeve 37 in the direction of arrow B to the member 31. In another embodiment, the outward motion is caused by moving the sleeve 37 in a distal direction.

In one embodiment, rod 20 and inserter 30 continue to move downward into the guide 40a while rod 20 is pivoted outward. In one embodiment, the pivoting motion of the rod 20 may begin when the first end 21 of the rod 20 is aligned with a top edge of the slot 41. In another embodiment, outward motion begins when the second end 22 of the rod 20 is aligned with a top edge of the slot 41. In another embodiment, the pivoting motion begins when the first end 21 nears the anchor 100.

Figure 4D:
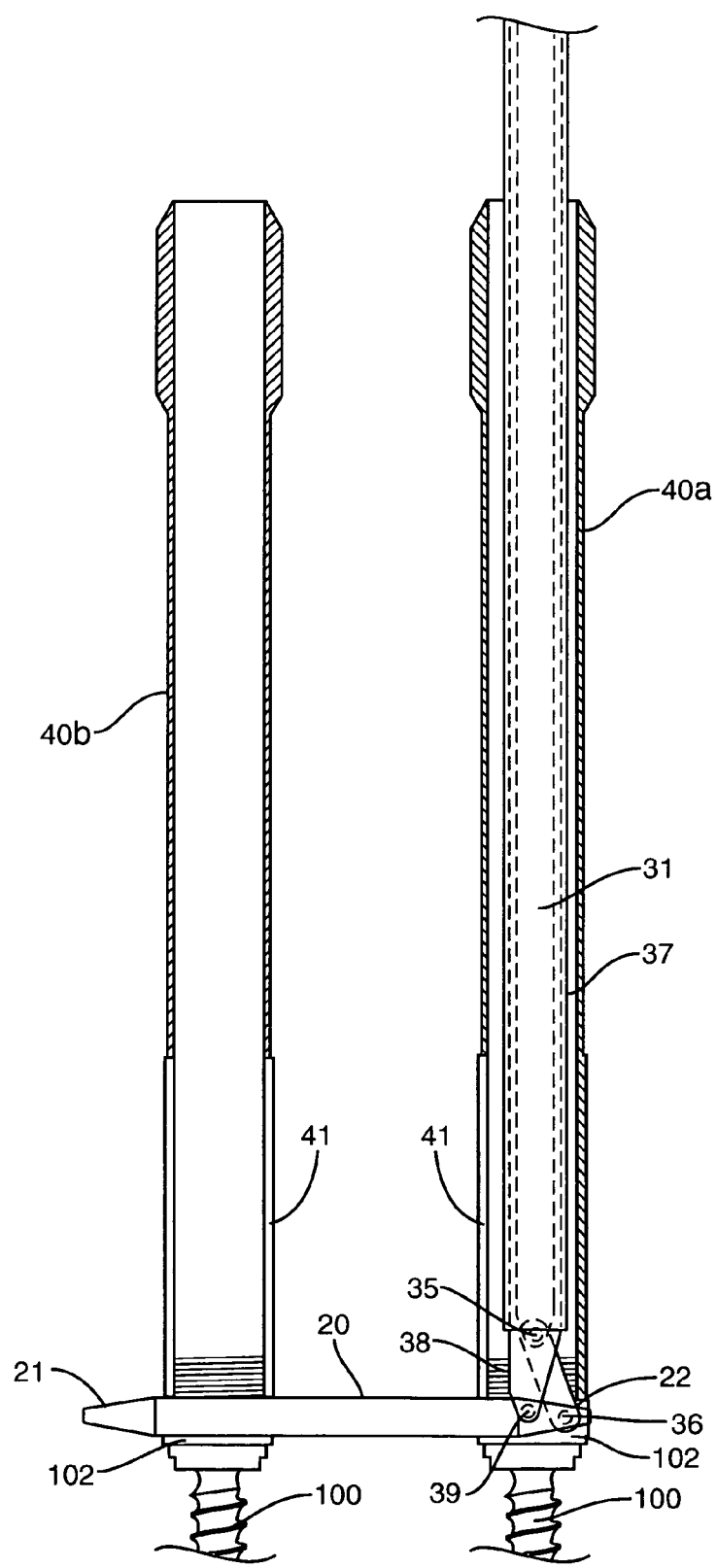

As illustrated in FIGS. 4C and 4D, the pivoting motion causes the first end 21 of the rod 20 to approach the second anchor 100 associated with guide 40b. Guide 40b may also include a slot 41 to allow the first end 21 to move over the anchor 100. Slots 41 may extend through a single section of the sidewall of the guides 40a, 40b, or may extend through two or more sections of the sidewall. In one embodiment as illustrated in FIG. 4D, rod 20 passes through both guides 40a, 40b. In one embodiment, the tapered shape of the first end 21 eases the movement through the body as the rod 20 pivots outward from the guide 40a.

As illustrated in the embodiment of FIG. 4D, rod 20 may be pivoted outward to a position that is substantially perpendicular to the inserter 30. The inserter 30 continues to move down the guide 40a causing the rod 20 to seat within the anchors 100. Specifically, a portion of the rod 20 adjacent to the first end 21 seats within the channel 102 of the first anchor 100, and a portion of the rod 20 adjacent to the second end 22 seats within the channel 102 of the second anchor 100. The placement of the rod 20 within the anchors 100 may vary depending upon the context. In one embodiment, both anchors are positioned towards a middle portion of the rod 20. In one embodiment, both anchors are positioned in proximity to one of the ends 21, 22. In other embodiments, the rod 20 seats within more than two anchors 100.

Figure 4E:
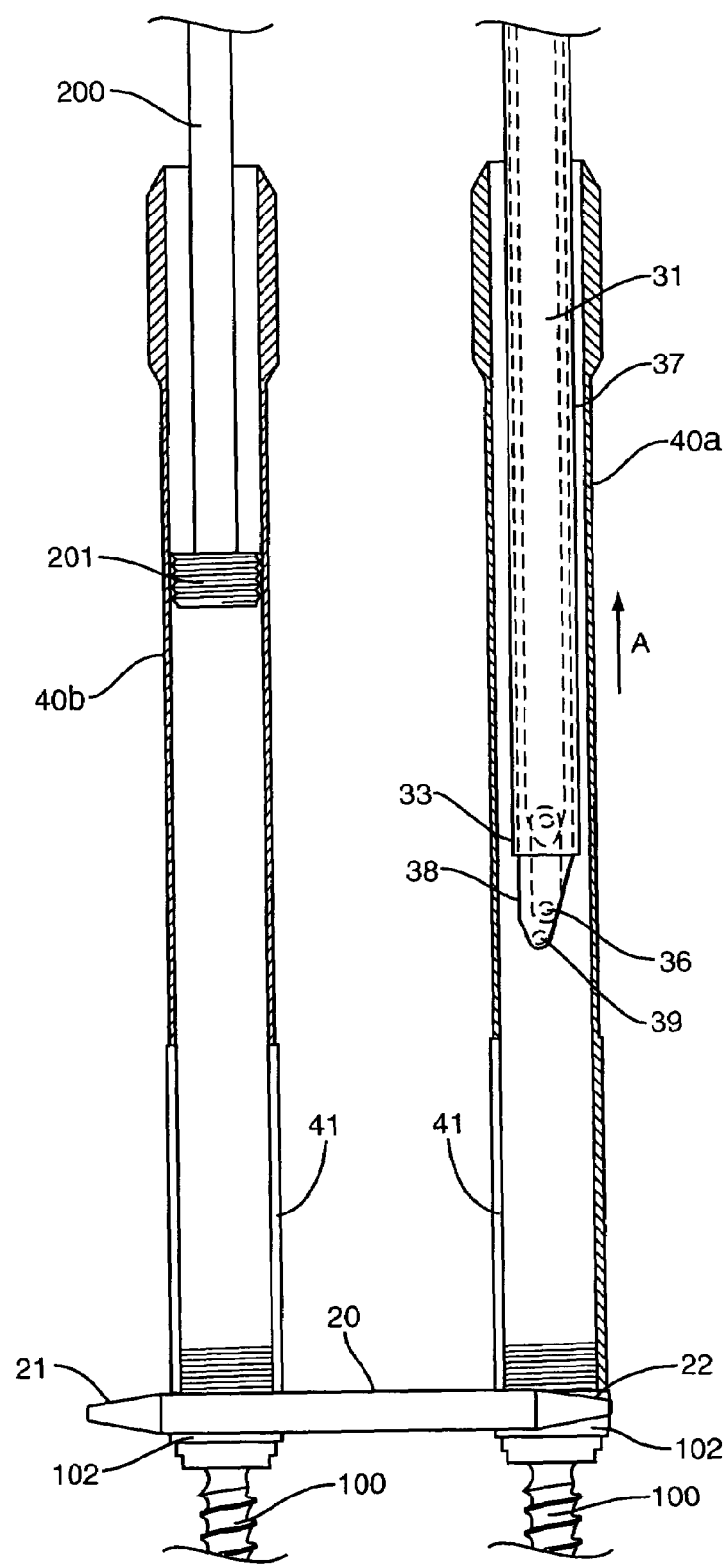

After the rod 20 is seated to the anchors 100, inserter 30 is removed from the rod 20 as illustrated in FIG. 4E. In one embodiment, an upward force applied to the inserter 30 in the direction of arrow A causes the connectors 36, 39 to release from the rod 20. This allows the rod 20 to remain within the anchors 100, and for the inserter 30 to be removed from the guide 40a. Guides 40a, 40b may also be used for attaching the rod 20 within the anchors 100. In one embodiment, guides 40a, 40b provide conduits for inserting fasteners 201. In one embodiment, an insertion tool 200 having an elongated body 202 moves fasteners 201 through the guides 40a, 40b and connects the rod 20 to the anchors 100.

Figure 5A:
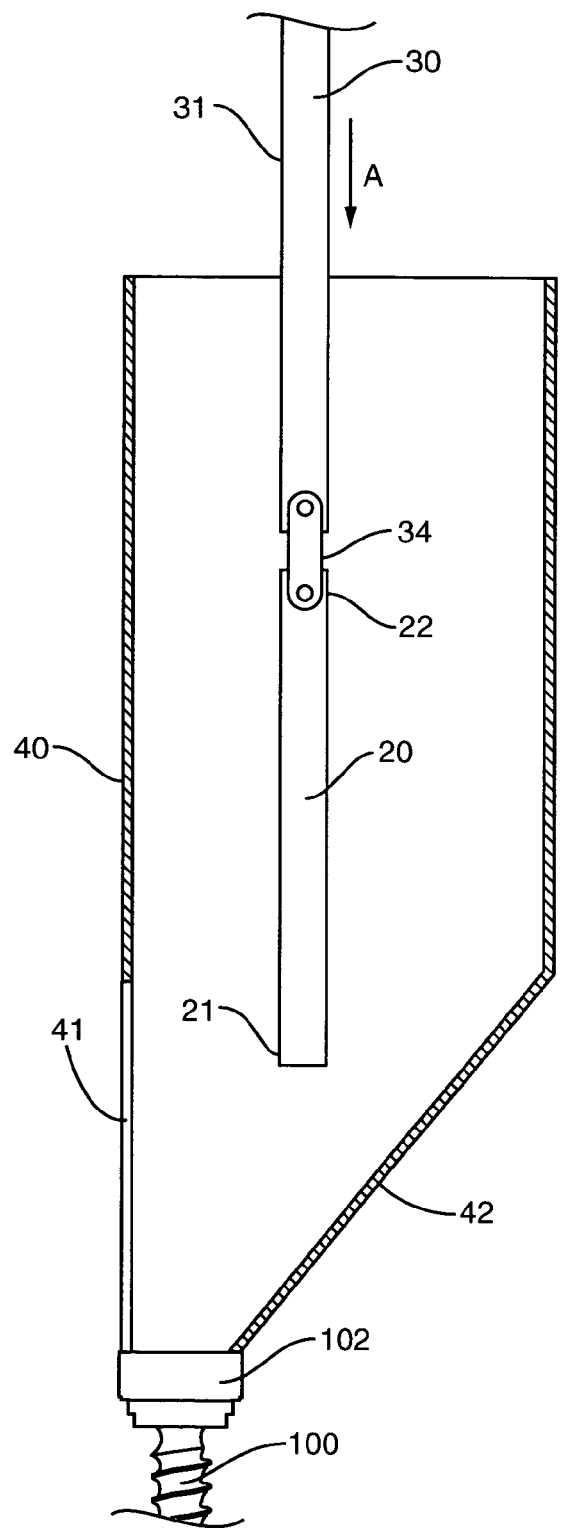
FIGS. 5A-D are side views of inserting a rod to an anchor according to one embodiment.

FIGS. 5A-5D illustrate another embodiment. Inserter 30 includes a member 31 having an arm 34 that attaches to the rod 20 at connector 36. In this embodiment, inserter 30 does not include an outer sleeve. Guide 40 has a larger width and includes a ramped section 42 at the distal end. The ramped section 42 may be positioned at a variety of angles. In one embodiment, the ramped section 42 has a continuous slope. In another embodiment, ramped section 42 includes a variable slope. In one embodiment as illustrated in FIG. 5A, ramped section 42 terminates at the anchor 100. In another embodiment, ramped section 42 terminates at a point laterally offset from the anchor 100. As illustrated in FIG. 5A, inserter 30 with the rod 20 attached are moved downward into the guide in the direction of arrow A. In this initial orientation, the rod 20 and inserter 30 are coaxially aligned. In another embodiment, the rod 20 is angled outward relative to the inserter 30 but still sized to fit within the guide 40.

Figure 5B:
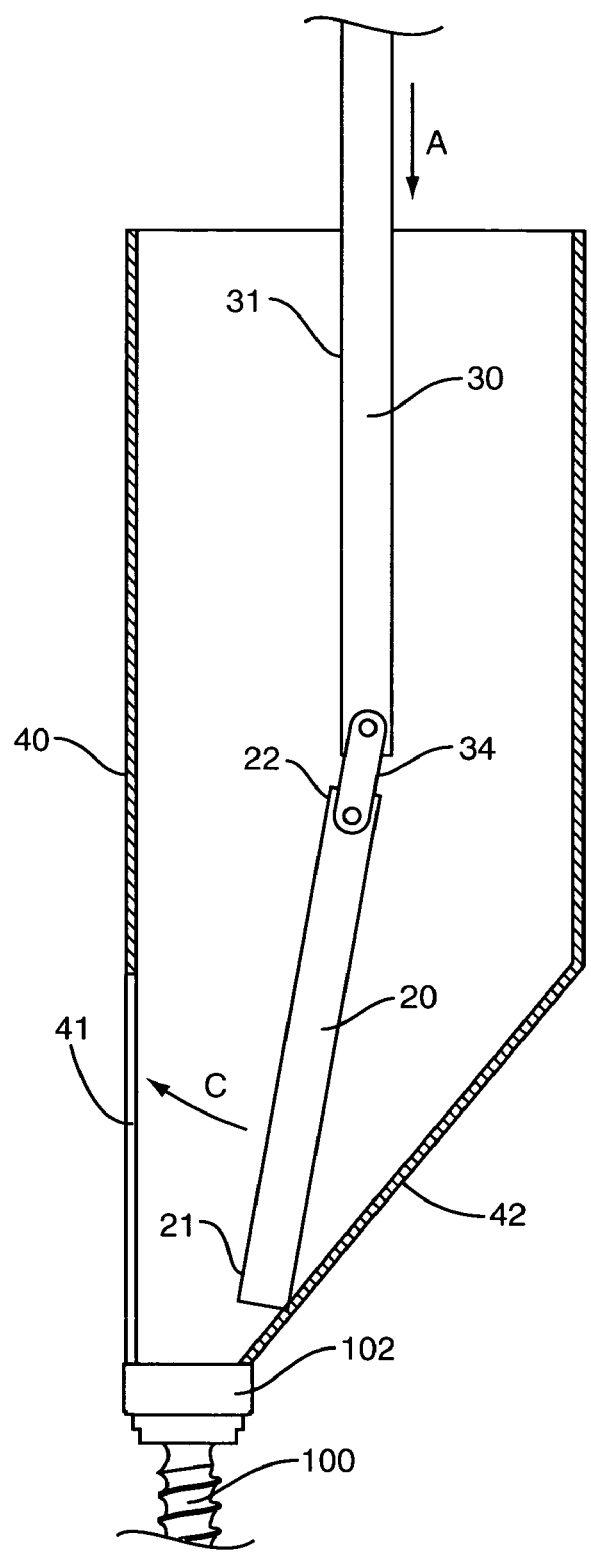

As the inserter 30 and rod 20 travel down the guide 40, the first end 21 of the rod 20 contacts the ramped section 42 causing the rod 20 to pivot outward as illustrated in FIG. 5B. Continued movement of the inserter 30 in the direction of arrow A causes the first end 21 to slide along the ramped section 42. As the distal end of the inserter 30 nears the start of the ramped section 42, the outward angle of the rod 20 increases.

Figure 5C:
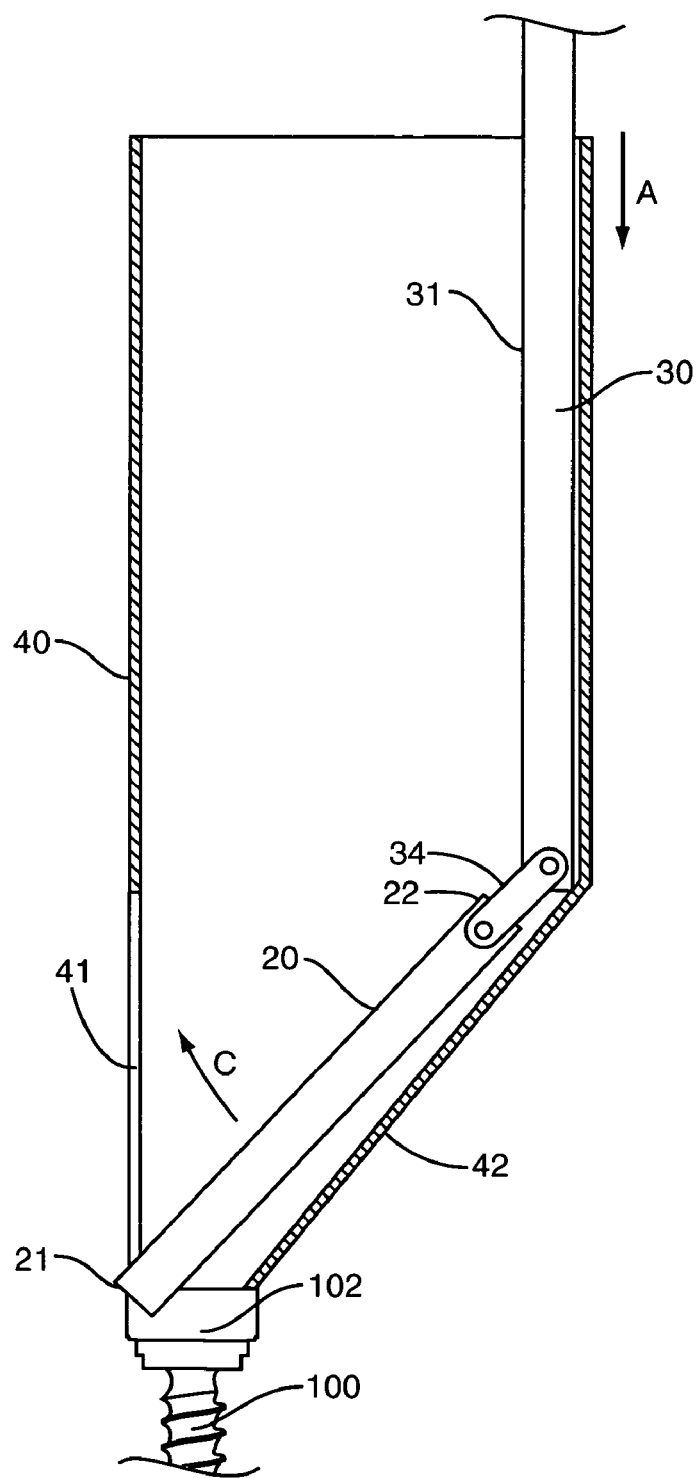
Figure 5D:
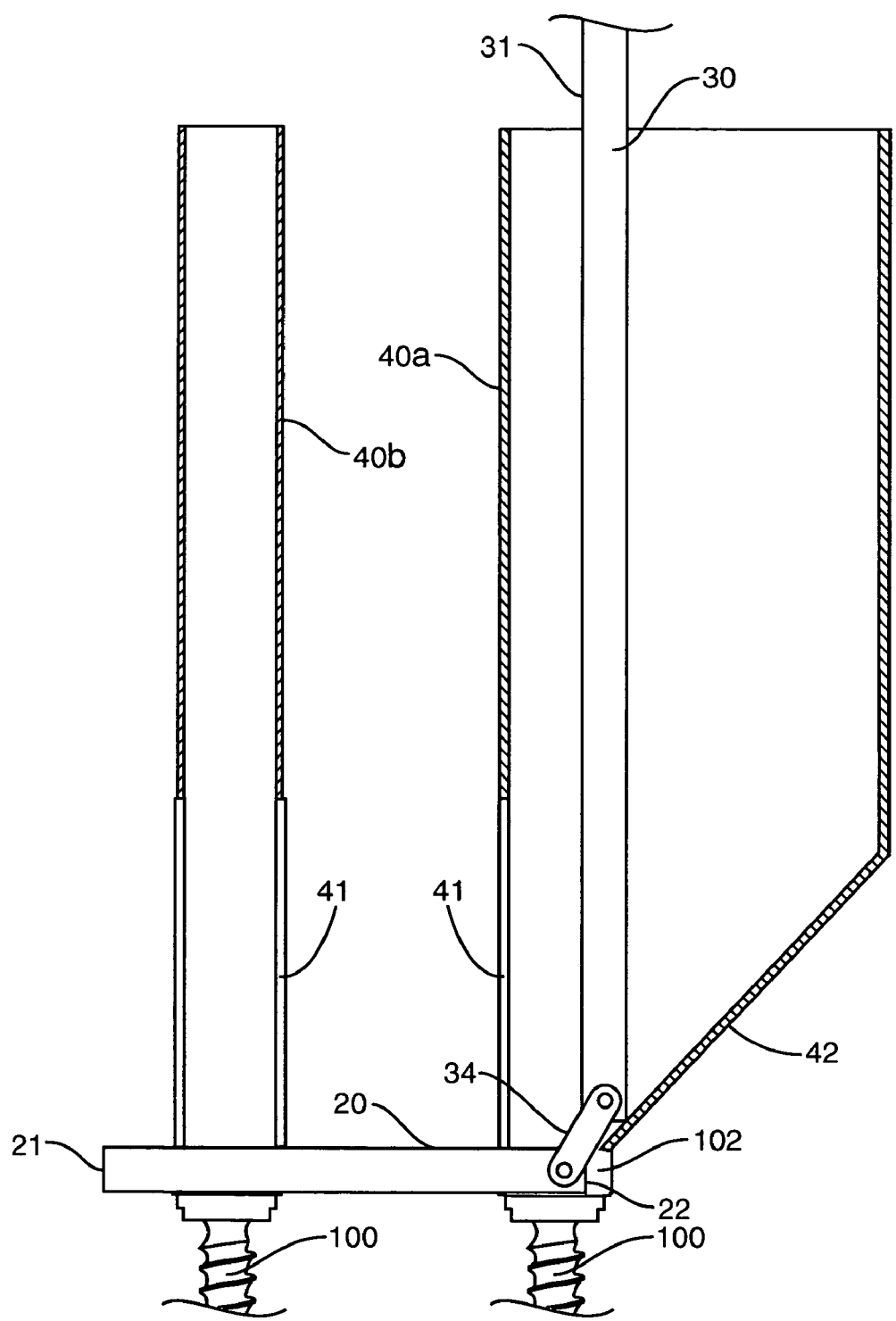

As the rod 20 and inserter 30 continue to move, the first end 21 slides along the ramped section 42. In one embodiment as illustrated in FIG. 5C, the first end 21 may further slide across the anchor 100. As illustrated in FIG. 5D, continued movement may result in the inserter distal end 33 sliding along the ramped section 42. At this position, rod 20 may be substantially perpendicular to the inserter 30. Inserter 30 is moved downward into the guide 40 until the rod 20 seats within the anchor 100. The inserter 30 may then be detached from the rod 20 and removed from the guide 40.

Figure 6:
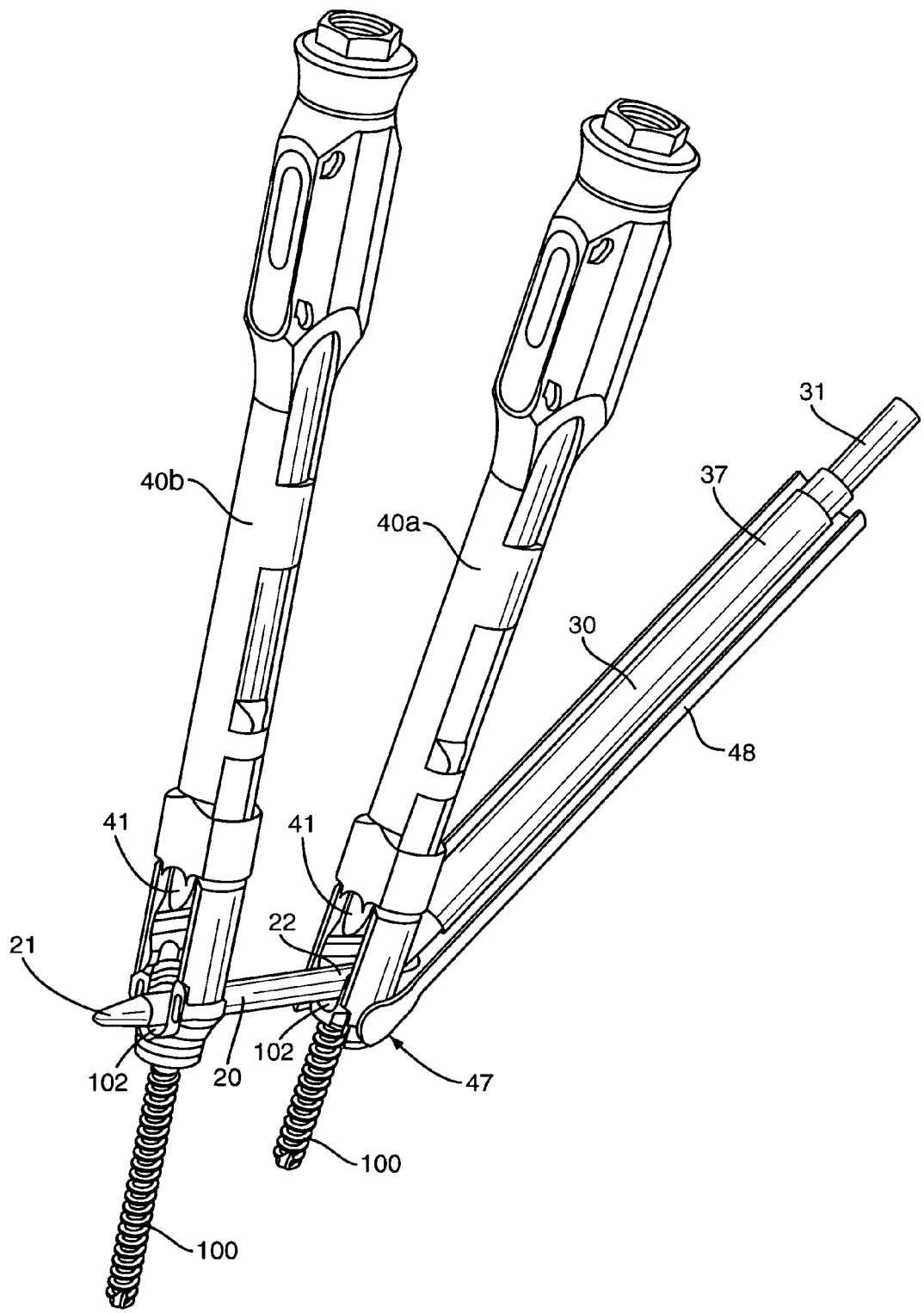
FIG. 6 is a perspective view of a rod extending between anchors according to one embodiment.

FIG. 6 illustrates another embodiment having a door 48. Door 48 has an elongated body that extends between first and second ends. In one embodiment as illustrated in FIG. 6, door 48 has a curved cross-sectional shape forming a substantially U-shape that is sized to guide the inserter 30 and rod 20. In another embodiment, door 48 forms an enclosed section through which the inserter 30 and rod 20 are inserted. The door 48 is positioned adjacent to the slot 41 in the guide 40a to allow the inserter 30 and rod 20 to be moved to the anchor 100.

In one embodiment, door 48 is attached after the guide 40a is positioned in the patient. Door 48 is inserted into the patient through a separate incision from the guide 40a. The first end of the door 48 is positioned adjacent to the distal end of the guide 40a. In one embodiment, door 48 includes a connection 47 that connects the door 48 to the guide 40a.

In another embodiment, door 48 is mounted to the guide 40a prior to insertion into the patient. The door 48 and the guide 40a are inserted together into the patient. In one embodiment, door 48 is movably mounted to the guide 40a. A connection 47 attaches the first end of the door to the distal end of the guide 40a. The door 48 may attach directly at the distal end of the guide 40a, or may be spaced upward on the guide 40a but within proximity to the distal end. The connection 47 provides for the door 48 to pivotally move between a first, extended position as illustrated in FIG. 6, and a second, closed position with the door 48 in proximity to the guide 40a. In one embodiment, the U-shaped door 48 cradles around the guide 40a when the door 48 is in the second, closed position.

In one embodiment, the guide 40a and attached door 48 are inserted into the patient when the door 48 is in the closed position. After insertion, the door 48 is moved to the first, extended position. After the rod 20 is positioned in the anchors 100 and the inserter 30 is detached and removed from the patient, the door 48 is returned to the closed position. The door 48 and guide 40a are then removed from the patient when the door 48 is closed. In one embodiment, door 48 is non-movable and remains in the open position.

The door 48 is aligned at an angle relative to the anchors 100 to reduce the amount of outward movement necessary for the rod 20 to move relative to the inserter 30. In the previous embodiments described for FIGS. 4 and 5, the rod 20 moves to be substantially perpendicular to the inserter 30. With the door 48, the amount of movement is reduced. In one embodiment, the door 48 is at an angle of about 45° relative to the anchor 100. Therefore, the rod 20 moves about 45° during insertion to extend across the anchors 100.

The term "distal" is generally defined as in the direction of the patient, or away from a user of a device. Conversely, "proximal" generally means away from the patient, or toward the user. Spatially relative terms such as "under ", "below ", "lower ", "over ", "upper ", and the like, are used for ease of description to explain the positioning of one element relative to a second element. These terms are intended to encompass different orientations of the device in addition to different orientations than those depicted in the figures. Further, terms such as "first ", "second ", and the like, are also used to describe various elements, regions, sections, etc and are also not intended to be limiting. Like terms refer to like elements throughout the description.

As used herein, the terms "having ", "containing ", "including ", "comprising" and the like are open ended terms that indicate the presence of stated elements or features, but do not preclude additional elements or features. The articles "a ", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of positioning a rod within an anchor in a patient, the method comprising the steps of:

attaching a rod to a distal end of an inserter by attaching a first section of the inserter at a first axial point along the rod and a second section of the inserter at a second axial point along the rod that is axially offset from the first axial point and coaxially aligning the rod with the inserter;

moving the rod and the inserter into the patient with the rod and inserter coaxially aligned;

after moving the rod and inserter a distance into the patient, axially moving the first section of the inserter relative to the second section and pivoting the first axial point about the second axial point and pivoting a first end of the rod outward from the inserter;

positioning the rod into the anchor while the rod is pivoted outward from the inserter; and detaching the rod from the inserter while positioned in the anchor and removing the inserter from the patient.

2. The method of claim 1, wherein the step of moving the rod and the inserter into the patient comprises moving the rod and inserter through an interior section of a guide that is inserted within the patient.

3. The method of claim 2, further comprising pivoting the rod outward from the inserter and through a slot in the guide.

4. The method of claim 1, further comprising pivoting the rod outward from the inserter an amount to be substantially perpendicular to the inserter and positioning the rod into the anchor.

5. The method of claim 1, further comprising detaching the rod from the inserter when the rod is substantially perpendicular to the inserter.

6. The method of claim 1, wherein the step of moving the rod and the inserter into the patient is performed percutaneously.

7. The method of claim 1, further comprising simultaneously moving the rod into the patient and pivoting the rod outward from the inserter.

8. The method of claim 1, wherein the step of moving the rod and inserter into the patient comprises moving the rod and inserter along a door and into a guide.

9. A method of positioning a rod within an anchor in a patient, the method comprising the steps of:
attaching a rod to a distal end of an inserter and coaxially aligning the rod with the inserter;
moving the rod and the inserter through an interior of a guide and into the patient a first distance with the rod and inserter coaxially aligned;
after moving the rod and inserter the first distance into the patient, pivoting a first connection point between the rod and the inserter about a second connection point between the rod and the inserter and pivoting a first end of the rod outward from the inserter with a first end of the rod moving through a slot in the guide;
positioning the rod into a first anchor that is aligned with the guide and the first end of the rod into a second anchor that is spaced away from the first anchor; and
removing the inserter from the rod and maintaining the rod in the first and second anchors.

10. The method of claim 9, further comprising moving the rod and inserter through the interior of the guide beyond the first distance and simultaneously pivoting the first end of the rod outward from the inserter.

11. The method of claim 9, further comprising pivoting the rod outward from the inserter about 90° and positioning the rod into the first and second anchors.

12. A method of positioning a rod within an anchor in a patient, the method comprising the steps of:
moving a rod positioned at a distal end of an inserter into an elongated guide while an axis of the rod is parallel with an axis of the inserter, the inserter including an elongated member that is operatively connected to the rod at a first point along the rod and an exterior sleeve that encircles the inserter and is operatively connected to the rod at a second point along the rod that is axially offset from the first point;
moving the rod a distance along the guide;
axially moving one of the exterior sleeve and the inserter relative to the other thereby moving one of the first and second points away from the axis of the inserter and pivoting the rod about the other of the first and second points;
positioning the rod into the anchor while the rod is pivoted relative to the inserter; and
detaching the rod from the inserter.

13. The method of claim 12, further comprising moving the elongated member in a distal direction relative to the inserter and moving the first point away from the axis of the inserter and pivoting the rod about the second point.

14. The method of claim 12, further comprising contacting a distal end of the rod against an inclined slope on an interior of the guide and pivoting the rod.

15. The method of claim 12, further comprising pivoting the rod and moving a distal end of the rod through a slot at a distal end of the guide.

16. The method of claim 12, further comprising pivoting the rod and positioned the rod into a second anchor that is spaced away from the anchor.

17. The method of claim 12, further comprising moving the rod and the inserter into the elongated guide while the rod and the inserter are coaxially aligned.

18. The method of claim 12, further comprising pivoting the rod to be perpendicular to the inserter prior to detaching the rod from the inserter.

19. A method of positioning a rod within an anchor in a patient, the method comprising the steps of:
simultaneously moving a rod and an inserter into the patient with the rod and the inserter coaxially aligned;
after moving the rod and inserter a distance into the patient, axially moving an inner member of the inserter attached to the rod at a first axial point relative to an outer member of the inserter attached to the rod at a second axial point that is axially offset from the first axial point and pivoting a first end of the rod outward from the inserter;
continuing to move the rod and the inserter into the patient beyond the distance and pivoting the rod to be perpendicular to the inserter; and
positioning the rod into the anchor while the rod is perpendicular to the inserter.

20. The method of claim 19, further comprising detaching the rod from the inserter while positioned in the anchor and removing the inserter from the patient.

* * * * *